(12) United States Patent
Bellier et al.

(10) Patent No.: US 11,306,294 B2
(45) Date of Patent: Apr. 19, 2022

(54) VIRUS-LIKE PARTICLES WHICH CAN BE USED IN THE TREATMENT OF AUTOIMMUNE DISEASES

(71) Applicants: Sorbonne Universite, Paris (FR); INSERM (Institut National de la Santé et de la Recherche Médicale), Paris (FR); Assistance Publique—Hôpitaux de Paris, Paris (FR)

(72) Inventors: Bertrand Bellier, Paris (FR); David Klatzmann, Paris (FR)

(73) Assignees: Sorbonne Universite, Paris (FR); INSERM (Institut National De La Sante Et De La Recherche Medicale), Paris (FR); Assistance Publique—Hopitaux De Paris, Paris (FR)

( * ) Notice: Subject to any disclaimer, the term of this patent is extended or adjusted under 35 U.S.C. 154(b) by 0 days.

(21) Appl. No.: 16/759,125

(22) PCT Filed: Oct. 26, 2018

(86) PCT No.: PCT/FR2018/052676
§ 371 (c)(1),
(2) Date: Apr. 24, 2020

(87) PCT Pub. No.: WO2019/081873
PCT Pub. Date: May 2, 2019

(65) Prior Publication Data
US 2020/0347363 A1 Nov. 5, 2020

(30) Foreign Application Priority Data
Oct. 26, 2017 (FR) ........................ 1760110

(51) Int. Cl.
*A61K 39/00* (2006.01)
*A61K 38/17* (2006.01)
*A61K 39/12* (2006.01)
*A61K 9/00* (2006.01)
*A61K 39/385* (2006.01)
*C12N 7/00* (2006.01)
*A61P 29/00* (2006.01)
*C12N 15/86* (2006.01)
*A61P 37/08* (2006.01)
*A61K 35/76* (2015.01)
*C07K 14/005* (2006.01)
*C07K 14/705* (2006.01)
*A61K 35/12* (2015.01)

(52) U.S. Cl.
CPC ............... *C12N 7/00* (2013.01); *A61K 35/76* (2013.01); *A61P 29/00* (2018.01); *A61P 37/08* (2018.01); *C07K 14/005* (2013.01); *C07K 14/70521* (2013.01); *C07K 14/70578* (2013.01); *C12N 15/86* (2013.01); *A61K 2035/122* (2013.01); *C12N 2740/13023* (2013.01); *C12N 2740/16023* (2013.01); *C12N 2740/16043* (2013.01)

(58) Field of Classification Search
CPC ............ A61K 2300/00; A61K 38/1774; A61K 38/177; A61K 39/12; Y02A 50/30
See application file for complete search history.

(56) References Cited

FOREIGN PATENT DOCUMENTS

| WO | WO-2008/130382 A2 | 10/2008 |
| WO | WO2008130382 | * 10/2008 |
| WO | WO-2016/128542 A1 | 8/2016 |
| WO | WO2016128542 | * 8/2016 |

* cited by examiner

*Primary Examiner* — Barry A Chestnut
(74) *Attorney, Agent, or Firm* — Cesari & McKenna, LLP

(57) ABSTRACT

The invention relates to a virus-like particle comprising an autoantigen and an immunoregulatory molecule exposed on its surface. The invention also relates to the use of said particle in the treatment of an autoimmune disease.

13 Claims, 11 Drawing Sheets
Specification includes a Sequence Listing.

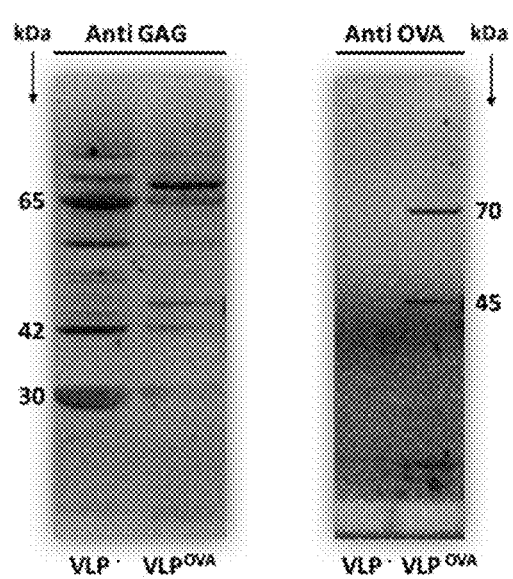
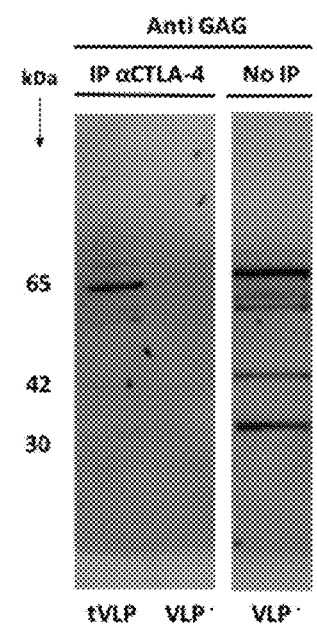
FIG. 3A
FIG. 3B
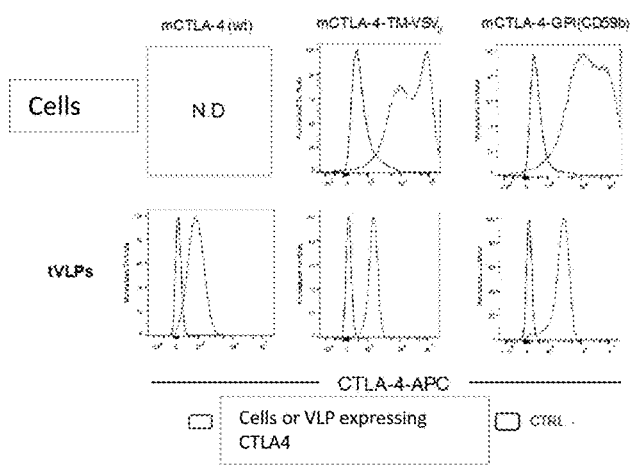
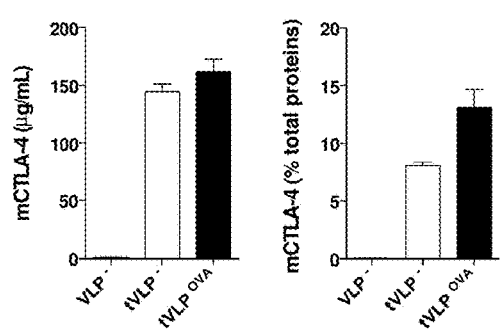
FIG. 3C
FIG. 3D

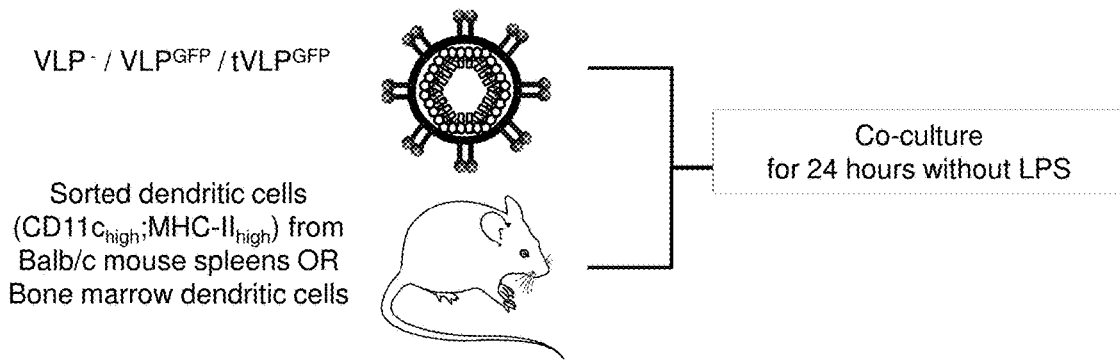
FIG. 4A
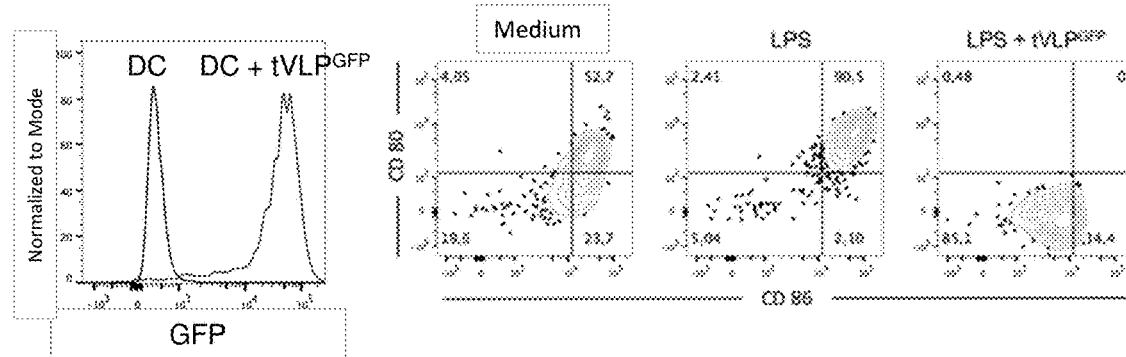
FIG. 4B
FIG. 4C
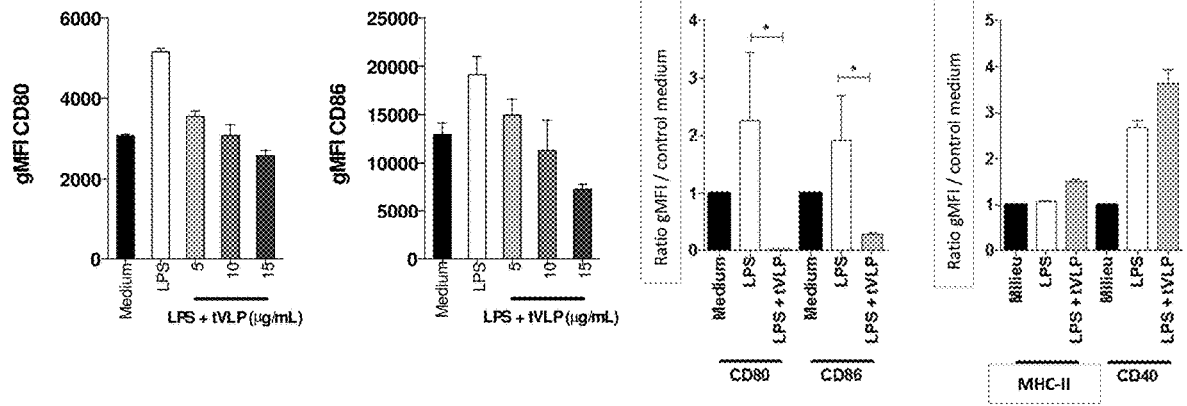
FIG. 4D
FIG. 4E

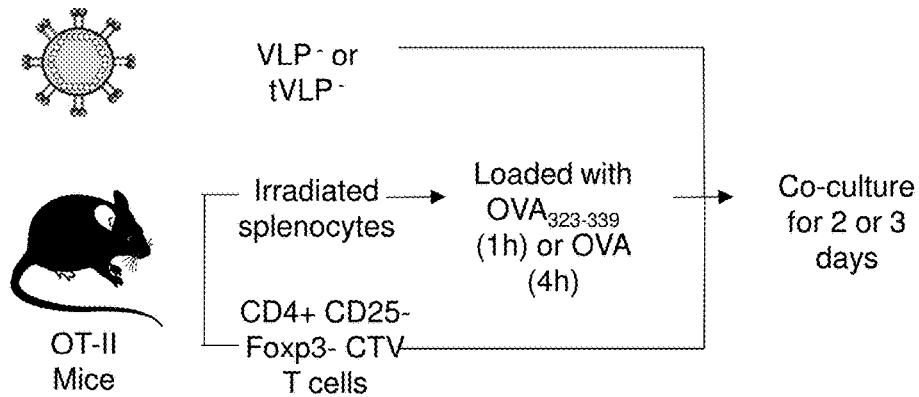
FIG. 6A
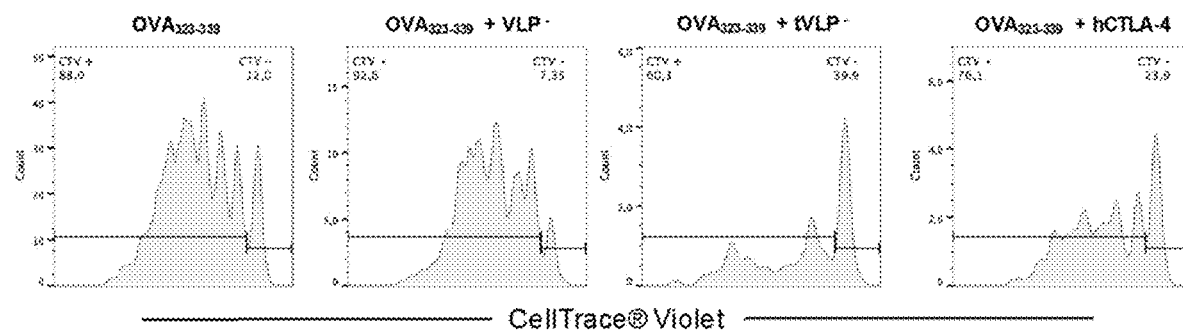
FIG. 6B
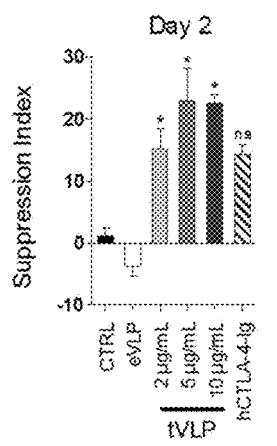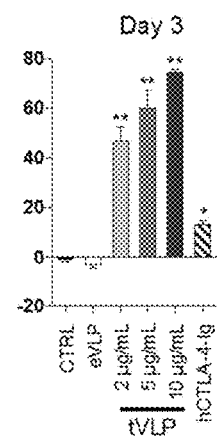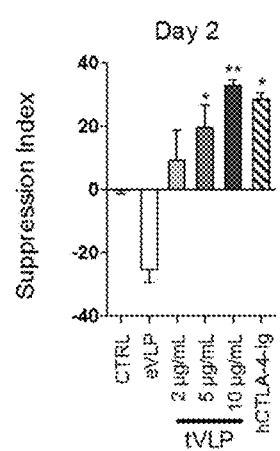
FIG. 6C  FIG. 6D

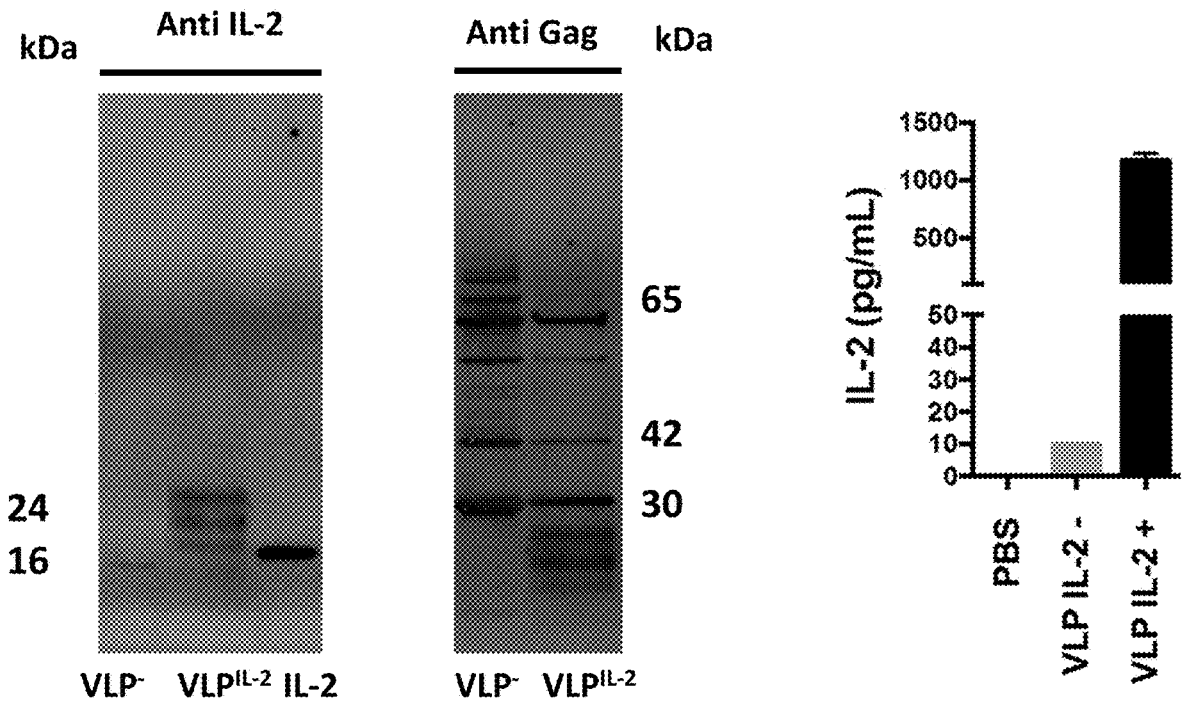
FIG. 8A
FIG. 8B
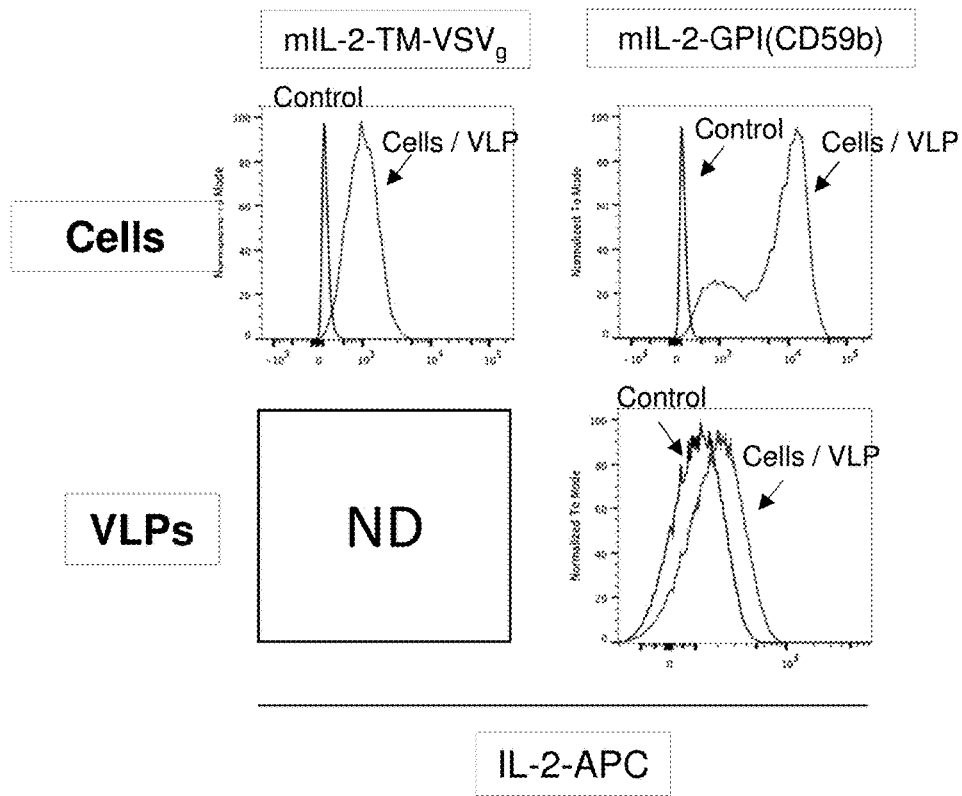
FIG. 8C

VIRUS-LIKE PARTICLES WHICH CAN BE USED IN THE TREATMENT OF AUTOIMMUNE DISEASES

CROSS-REFERENCE TO RELATED APPLICATIONS

This application is the National Stage of International Application No. PCT/FR2018/052676, filed Oct. 26, 2018, which claims the benefit of priority of French Patent Application No. 1760110, filed Oct. 26, 2017, the contents of both being incorporated by reference in their entirety for all purposes.

FIELD OF THE INVENTION

The invention relates to compositions comprising virus-like particles useful for modifying, regulating or suppressing an immune response, more particularly for treating an immune dysfunction such as an autoimmune disease. Methods for producing said compositions are described. This invention can be used in mammals, in particular in humans but also in other vertebrates.

PRIOR ART

The prevalence of autoimmune diseases has increased considerably in industrialized countries in recent decades. Autoimmune diseases result from a dysfunction of the immune system that attacks the normal constituents of the body (autoantigen).

Today, treatments for autoimmune diseases are based on the use of immunosuppressive drugs and act non-specifically on the immune system, with consequences for its functionality and the effectiveness of anti-infective responses. The development of new effective, long-lasting and specific treatments for immune dysfunctions therefore remains necessary.

The administration of antigens that are the target of pathological mechanisms, in a formulation favorable to the establishment of immune tolerance, is a strategy of interest.

Virus-like particles (VLP) are used for anti-infectious or anti-tumor vaccination. Virus-like particles have the advantage that they can be easily modulated and can be used as an antigenic platform. Targeted antigens can thus be carried inside or on the surface of the virus-like particles, helping to trigger specific humoral and cellular immune responses, but also masking the antigens from neutralizing or reactive factors (antibodies) when they are inside. In addition, the great flexibility of this antigenic platform allows the vectorization of immunoregulatory molecules, which is at the origin of tolerance induction.

SUMMARY OF THE INVENTION

Interestingly, the inventors have shown that virus-like particles can block the activation of antigen presenting cells and the activation of T cells and can therefore be used to modulate immune responses or even induce specific immune tolerance. In other words, virus-like particles make it possible to make the body tolerant to the antigens vectorized by these so-called tolerogenic virus-like particles.

A first object of the invention is a virus-like particle comprising one or more antigen(s) and an immunoregulatory molecule exposed on the surface of the particle. The virus-like particle according to the invention is particularly used in the treatment of an immune dysfunction, preferably an autoimmune disease such as multiple sclerosis, type 1 diabetes, lupus, an autoimmune thyroid, Crohn's disease, rheumatoid arthritis, celiac disease, myasthenia gravis or Biermer's disease (autoimmune atrophic gastritis) or autoimmune hepatitis (AIH).

The virus-like particle is preferably in the form of a pharmaceutical composition further comprising a pharmaceutical excipient.

According to another aspect of the invention, a plasmid or set of plasmid(s) capable of producing in situ a virus-like particle as defined herein is used, in particular for their use in the treatment of immune dysfunction.

FIGURE LEGEND

FIGS. 3A-3D illustrate the characterization and expression of therapeutic proteins in $tVLP^{OVA}$. 3A. Western blot validation of Gag and OVA expression in virus-like particles $tVLP^{OVA}$. $VLP^-$ are control particles without OVA antigen. 3B. Validation by immunoprecipitation of CTLA-4 expression in tVLP virus-like particles. 3C. Comparison of the expression of chimeric forms of CTLA-4 (WT, TM-VSV-G, or GPI anchor domain) in transfected cells (top) or on the surface of virus-like particles (bottom) by flow cytometry. Non-transfected cells or $VLP^-$ are used as the negative control (black). 3D. Quantification of the CTLA-4 domain in tVLP, $tVLP^{OVA}$ or $VLP^-$ preparations by ELISA (left) and relative quantification of CTLA-4 to total proteins measured using the BCA method (right). Results are mean±SEM (n=4) and represent 3 independent experiments.

FIG. 4A-4E illustrate the uptake and effects of tVLP on purified dendritic cells. 4A. Experimental design. Purified $CD11c^{high}$ $MHC-II^{high}$ dendritic cells from the spleen of BALB/c mice or dendritic cells from bone marrow are cultured in the presence of $VLP^-$, $VLP^{GFP}$ or $tVLP^{GFP}$ and stimulated or not with LPS. Twenty-four hours after culture, the expression of co-stimulation molecules and activation markers is analyzed by flow cytometry. 4B. The uptake of $tVLP^{GFP}$ by purified dendritic cells is confirmed by the presence of GFP+ cells after 24 hours of culture. The $VLP^-$ are used as a negative control (black). (4C-4E). The expression of co-stimulation molecules and activation markers is analyzed by flow cytometry on purified dendritic cells after co-culture with medium in the presence or not of 1 μg/mL LPS and 5, 10 or 15 μg/mL $tVLP^{GFP}$. The expression of CD80, CD86, CD40 and MHC-II is analyzed in living cells expressing CD11c and MHC-II. 4C. Represents the cytometric profiles of CD80, CD86 in dendritic cells cultured in culture medium alone, in the presence of LPS and $tVLP^{GFP}$ (15 μg/mL). 4D. The expression of co-stimulation molecules is measured using the geometric mean fluorescence (MFI). 4E. Expression modulation is represented by the MFI ratio compared to the control medium.

Figure 1:
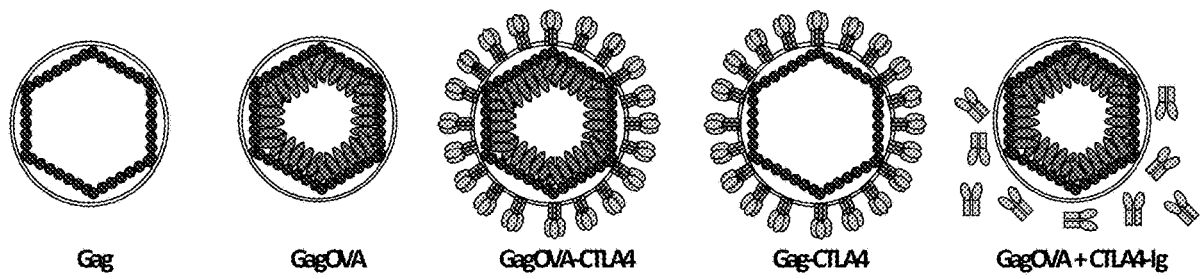
FIG. 1 illustrates the structure of VLP without antigen and without CTLA-4 (VLP), VLP with OVA antigen alone ($VLP^{OVA}$) or combined with CTLA-4 ($tVLP^{OVA}$), VLP without antigen and expressing CTLA-4 on its surface (tVLP–), and VLP with OVA antigen ($VLP^{OVA}$) co-injected with soluble CTLA-4 (CTLA-4-Ig).
Figure 2A:
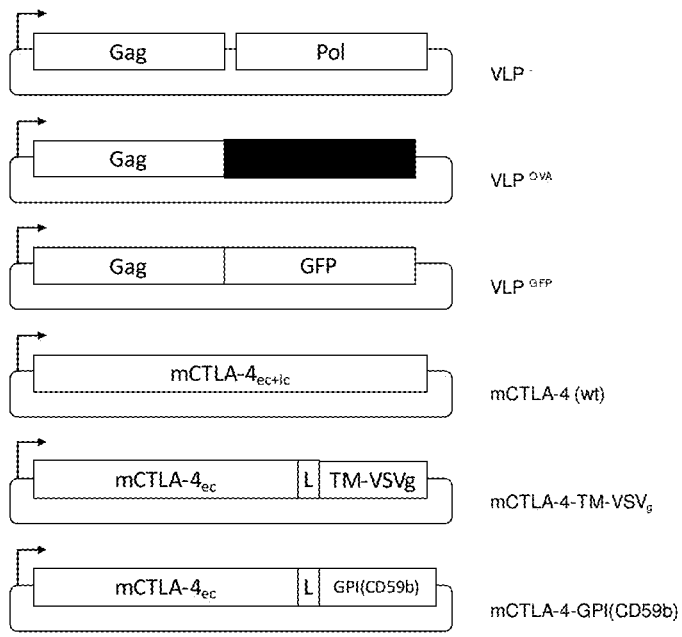
FIGS. 2A and 2B illustrate the constructs used to form the particles according to the invention (2A) and the structure of the tolerogenic virus-like particle $tVLP^{OVA}$ (2B) where OVA is the target antigen.
Figure 2B:
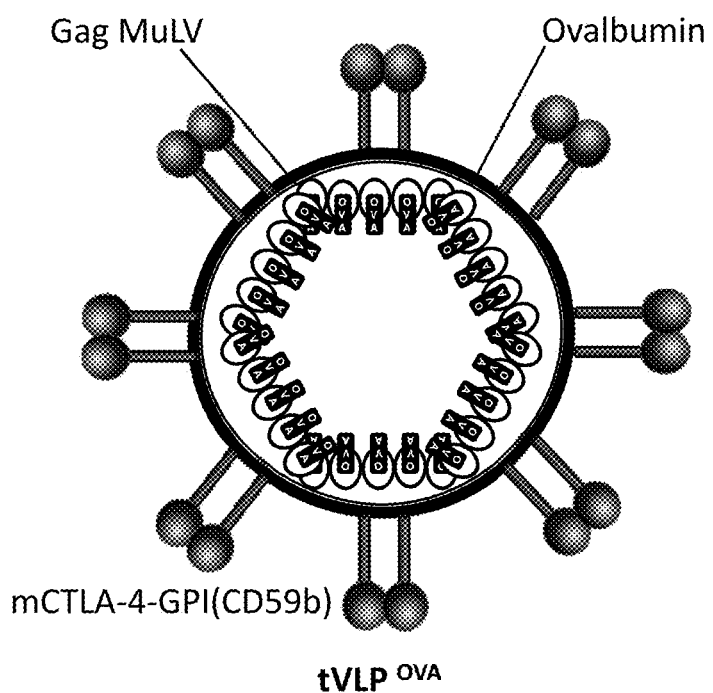
Figure 5A:
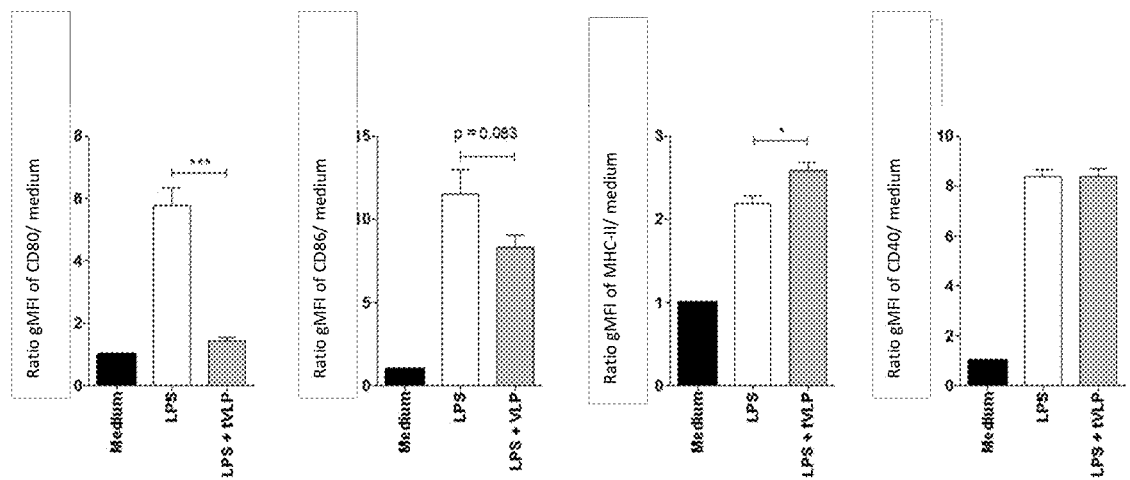
Figure 5B:
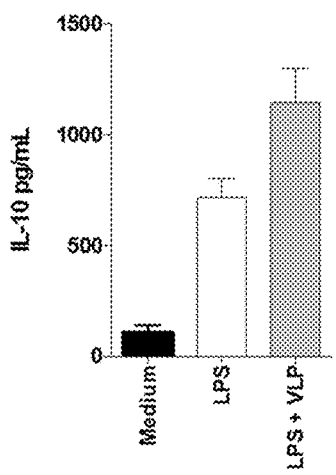

FIGS. 5A and 5B illustrate the effects of tVLP on dendritic cells derived from bone marrow precursors. 5A. illustrates CD80, CD86, CD40 and MHC-II expression analyzed by flow cytometry on live bone marrow-derived dendritic cells after co-culture with medium with or without the presence of 1 μg/mL LPS and 5, 10 or 15 μg/mL tVLP$^{GFP}$. The expression modulation of CD80, CD86, CD40 and MHC-II is represented by the gMFI ratio compared to the control medium. 5B. Quantification by ELISA of IL-10 in the culture supernatant of dendritic cells after 24 hours culture in medium alone, in the presence of LPS or in the presence of LPS and tVLP.

FIGS. 6A-6D illustrate the blocking of antigen-specific T cell proliferation by tVLP. 6A. Experimental design. CD4+ CD25− T cells from OT-II mice are cultured for 2-3 days with irradiated spleens from OT-II mice loaded with an OVA$_{323-339}$ peptide or OVA protein. To analyze proliferation, CD4+ OT-II T cells are labeled with CellTrace® Violet. Live OT-II CTV+CD4+ T cells co-cultured for 2 days with irradiated splenocytes loaded with an OVA$_{323-339}$ peptide in the presence or absence of 10 μg/mL of VLP$^-$, tVLP$^-$, or an equivalent dose of hCTLA-4 are analyzed by flow cytometry. 6B. Cytometric profile of CTV dilutions of CD4$^+$ CTV$^+$ OT-II T cells after two days under different culture conditions. (6C-6D). Suppression indices of CTV dilutions of OT-II cells co-cultured for two or three days with splenocytes contacted with OVA$_{323-339}$ peptide (6C) or OVA protein (6D). Results are mean±SEM (n=4) and represent 3 independent experiments.

FIGS. 7A-7E illustrate the validation of MOG expression in tVLP$^{MOG}$ and its suppressive effect on MS effector cells. 7A. Western blot validation of MOG and Gag expression in VLP$^{MOG}$. VLP$^-$ are used as a control. 7B. Flow cytometry validation of CTLA-4 expression in tVLP$^{MOG}$ virus-like particles. The VLP$-$ are used as a negative control. 7C. Blockage of proliferation of MOG-specific 2D2 T cells by tVLP$^{MOG}$. CTV dilution cytometry profile of CD4$^+$ CTV$^+$ 2D2 T cells after seven days in the presence of tVLP$^{MOG}$ and VLP$^-$ (control). 7D. Kinetics of T cell division under different culture conditions. 7E. Suppression indices and geometric means of CTV dilutions of 2D2 cells at 7 days of culture. Results are mean±SEM.

FIGS. 8A-8C illustrate the characterization and expression of therapeutic proteins in tVLP expressing IL-2 as an immunoregulatory molecule. 8A. Western blot validation of IL-2 and Gag expression in virus-like particles. 8B. Quantification of IL-2$^+$ in IL-2 and IL-2$^-$ VLP preparations by ELISA. 8C. Comparison of the expression of chimeric forms of IL-2 (TM-VSV-G or GPI anchor domain) in transfected cells (top) or on the surface of virus-like particles (bottom) by flow cytometry. Non-transfected cells or VLP$^-$ are used as the negative control (black).

Figure 9A:
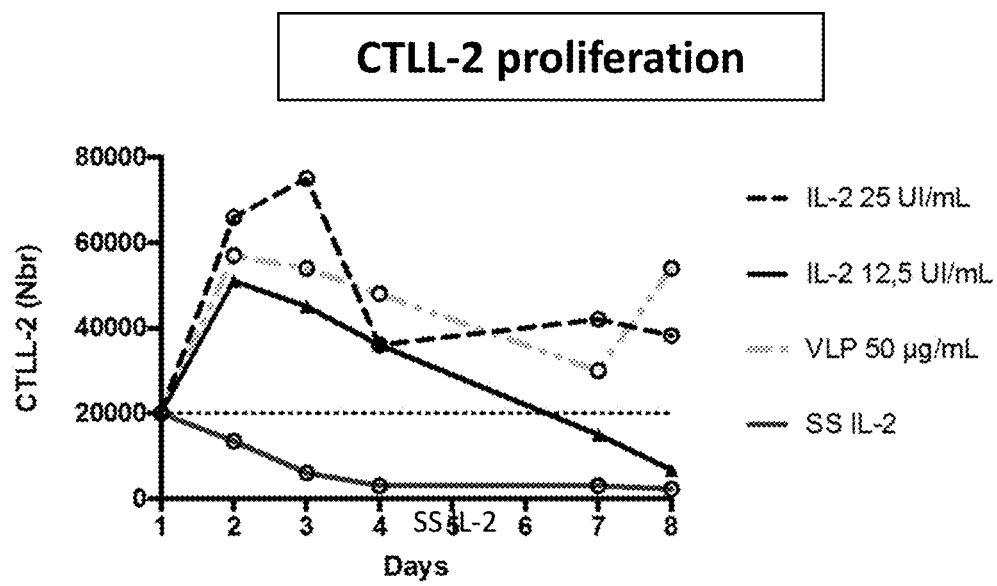
Figure 9B:
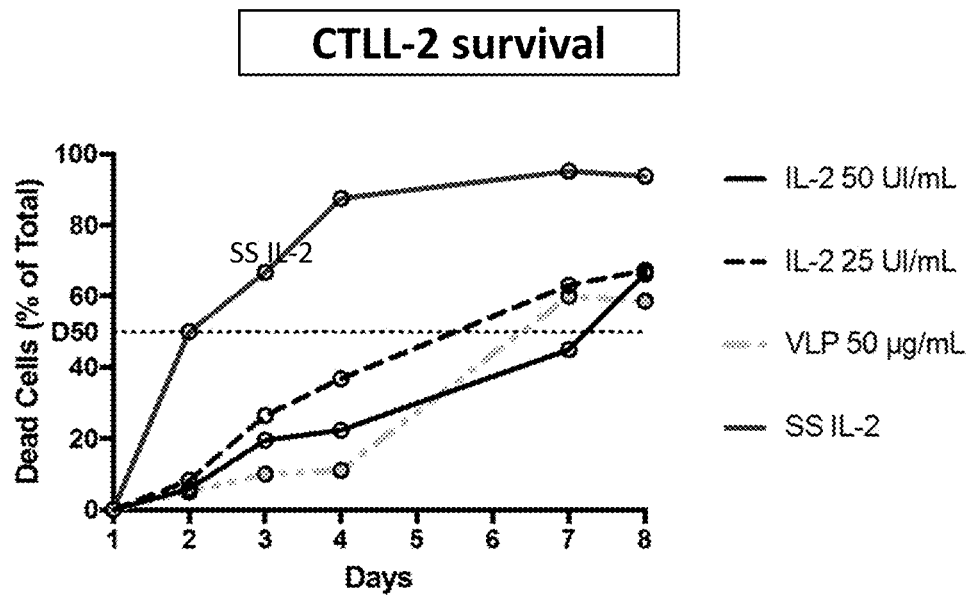

FIGS. 9A and 9B illustrate the functional validation of IL-2 present on the surface of tVLP. The IL-2+ VLP were cultured (50 μg/mL) with IL-2-dependent CTLL-2 cells. Cell proliferation (9A) and survival (9B) were evaluated over an 8-day period. In control, IL-2 at 25 or 50 IU/mL, or medium alone was used.

Figure 10:
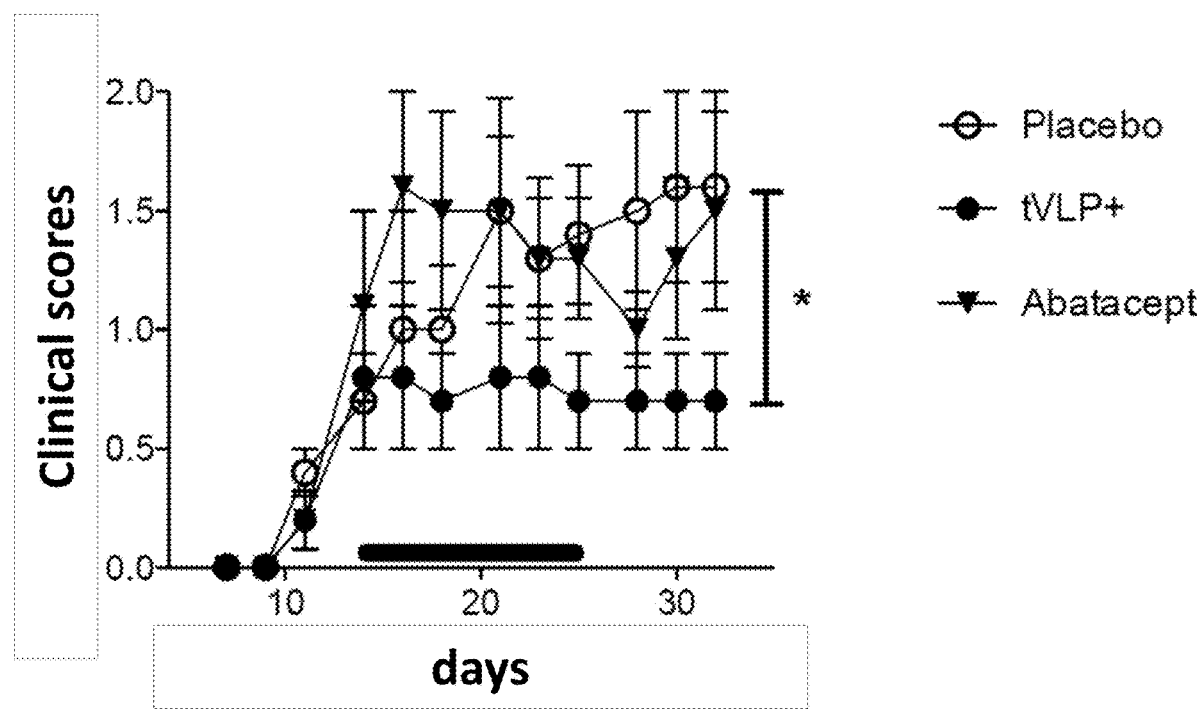

FIG. 10 shows the therapeutic effect of tVLPs in a mouse model of multiple sclerosis (mice developing experimental autoimmune encephalitis (EAE)). Clinical scores of EAE in mice treated with a daily dose of MOG antigen-specific vaccine (tVLP+), Abatacept or placebo between days 15 to 25 (in bold) after induction of EAE. Results are presented as means±standard deviation (n=5 mice/group). *, p<0.005; Mann-Whitney between tVLP+ and placebo.

Figure 11A:
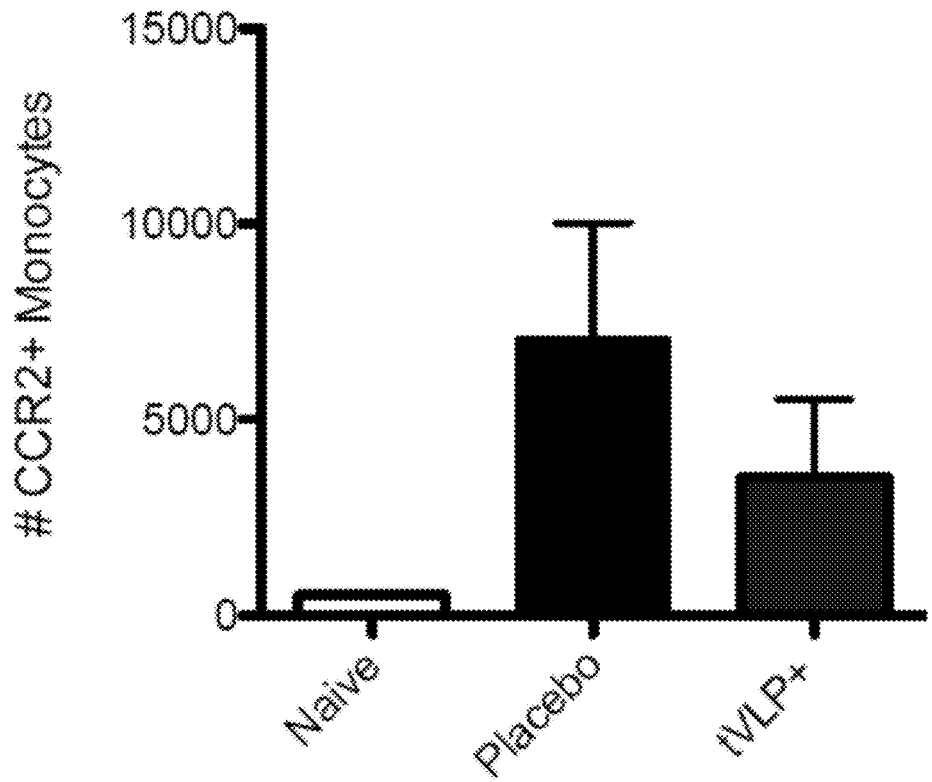
Figure 11B:
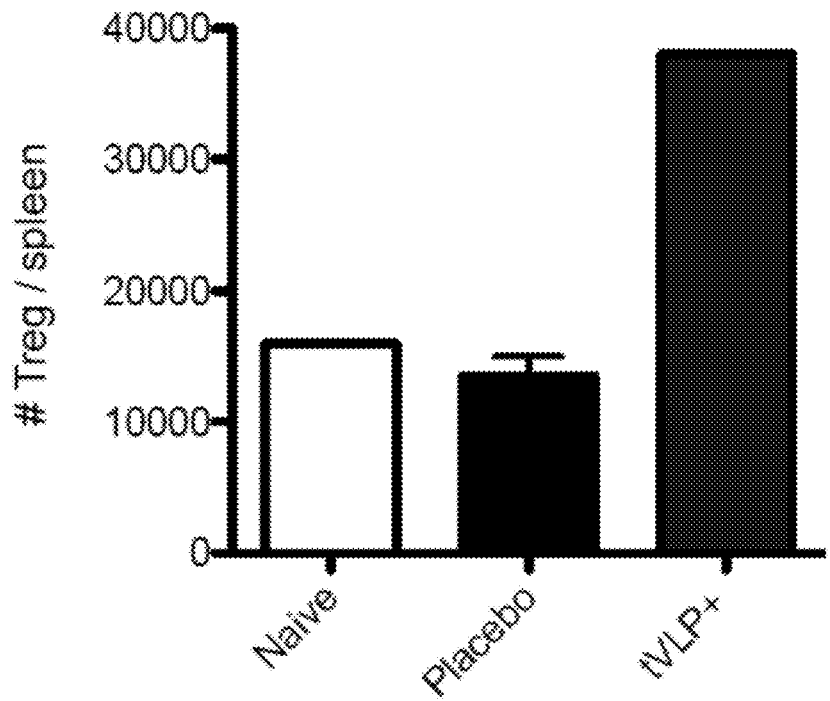

FIGS. 11A and 11B show that induction of tolerance by tVLPs reduces immune infiltration of the central nervous system and increases splenic Tregs. C57Bl/6 mice received daily intraperitoneal injection of tVLPs or PBS (placebo) between days 15 to 25 (in bold) after induction of EAE. On day 29, spleen and spinal/brain marrow were collected, and the infiltrating immune cells were isolated and analyzed by flow cytometry (FIG. 11A, inflammatory monocytes, FIG. 11B, Tregs lymphocytes). Naïve mice were included as controls. Results are presented in mean±standard deviation (n=2 mice/group).

DETAILED DESCRIPTION OF THE INVENTION

The inventors developed a method for treating immune dysfunctions in a subject, such as autoimmune diseases, comprising the administration of virus-like particles containing an antigen and an immunoregulatory molecule.

This virus-like particle advantageously contains an immunoregulatory molecule exposed on its surface.

The present invention therefore relates to a virus-like particle comprising an antigen and an immunoregulatory molecule exposed on the surface of the particle, which makes it possible to promote the specific tolerance of the antigen. The immunoregulatory molecule is preferably a molecule which exerts regulatory and/or suppressive functions on antigen presenting cells, promoting recruitment of regulatory T cells. In particular, the immunoregulatory molecule may be an immune-checkpoint receptor, more particularly a peptide sequence comprising the extracellular domain, more particularly the Ig-like domain of an immune-checkpoint receptor, preferably selected from the group consisting of: CTLA-4 (cytotoxic T-lymphocyte-associated protein 4), OX40 (tumor necrosis factor receptor superfamily, member 4 (TNFRSF4)), PD1 (programmed cell death 1), Tim3 (also known as HAVCR2), LAG-3 and TIGIT (also known as IVSTM3). The immunoregulatory molecule may also be a cytokine, preferably selected from the group consisting of: IL-2 (interleukin 2), IL-10 (interleukin 10) and TGF-beta. The immunoregulatory molecule is preferably fused to the transmembrane and/or anchoring domain of a protein, preferably a glycoprotein. In particular the immunoregulatory molecule is bound to the transmembrane domain of an envelope protein or a glycosylphosphatidylinositol (GPI) anchoring system to be exposed to the surface of the particle. The cytokine, which is preferably interleukin 2, may be human or from another animal species, it may be wild or mutant. In particular it may be a modified human IL-2 des-alanyl-1, serine-125.

It is possible to associate "adjuvant" molecules with the ability to direct immune responses towards a desired cytokine profile. A molecule capable of activating TLR (toll-like receptor) such as viral RNA, preferably non-coding RNA, can be associated to enhance Th1 responses (Pitoiset F. et al. J. Virol. 2017 Oct. 13; 91(21)) and thus combat Th2 responses that may sometimes be associated with autoimmune disease mechanisms, such as in autoimmune pancreatitis (Pakala et al., J Exp Med. 1997, 186(2): 299-306). The particles according to the invention may also be associated with molecules or adjuvants (alum-type) capable of initiating mechanisms that cause Th2-type responses.

The virus-like particle is preferably a synthetic retroviral particle. In other words, the virus-like particle comprises a retroviral capsid protein and/or a retroviral envelope protein.

The present invention relates more particularly to the virus-like particles defined herein, for use in the treatment of immune dysfunction.

The virus-like particles according to the invention are used for the treatment of autoimmune diseases.

The virus-like particle of said invention comprises an antigen which is a self-antigen also called autoantigen for use in the treatment of an autoimmune disease, preferably multiple sclerosis, type 1 diabetes, lupus, autoimmune thyroid disease, Crohn's disease, rheumatoid arthritis, celiac disease, myasthenia gravis or Biermer's disease (autoimmune atrophic gastritis) or autoimmune hepatitis (AIH).

Thus the administration of virus-like particles comprising the autoantigen makes it possible to induce specific tolerance to this antigen by inducing regulatory cells and suppressing the specific response and effector cells.

The present invention also relates to one or more plasmid(s) capable of producing virus-like particles in vitro and in situ. In particular, use is made of one or more plasmids encoding a capsid protein and/or an envelope protein constituting the virus-like particle. The present invention relates more particularly to said plasmids for use in the treatment of immune dysfunction.

The virus-like particle or the plasmid(s) capable of producing a virus-like particle in situ may be administered to the subject preferably by mucosal route, for example oral, sublingual, intranasal, subcutaneous or intravenous.

The present invention uses a pharmaceutical composition comprising the virus-like particle or plasmid(s) capable of producing virus-like particles in situ. This composition may also include a pharmaceutical excipient.

The pharmaceutical composition may comprise several virus-like particles or several plasmid(s) capable of producing in situ virus-like particles comprising different antigens and/or different immunoregulatory molecules.

Also described here is a method for preparing virus-like particles or plasmids capable of producing the virus-like particles in situ.

Definitions

The term "antigen" refers to a molecule such as a protein, polypeptide, peptide, lipid, nucleic acid, polysaccharide, epitope capable of being recognized by an antibody or cells of the immune system. In particular the antigen is capable of triggering an immune response. The immune response may lead to antibody production and/or activation of cells of the immune system. In particular, the antigen is a heterologous protein, polypeptide, peptide of the virus-like particle, especially a non-viral protein, polypeptide or peptide. In the context of the present invention, the antigen is a molecule heterologous to the virus forming the particle. It is preferably a non-viral molecule. In the invention, the antigen is a self-antigen also called autoantigen. The term "autoantigen" is used here to refer to a patient's own antigen that is targeted by an autoimmune response when tolerance is broken. The term also includes epitopic fragments of complete proteins.

An autoimmune disease is caused by an inappropriate response of the immune system against molecules or a combination of molecules that are normally present in the body. These molecules are then called autoantigens. Examples of autoimmune diseases are multiple sclerosis, type 1 diabetes, lupus, autoimmune thyroids, Crohn's disease, rheumatoid arthritis, celiac disease, myasthenia gravis or Biermer's disease (autoimmune atrophic gastritis) or autoimmune hepatitis (AIH).

Preferably, allergic reactions or allergic symptoms (such as rhinitis, allergic asthma, dermatitis, hives, sinus inflammation or anaphylactic shock following exposure to the allergen) are not included in the definition of autoimmune diseases covered here.

The term "treat" means to suppress symptoms, to eliminate the causes of the symptoms either transiently or permanently, but also to prevent or slow down the onset of symptoms of immune dysfunction.

The term "subject" means any human person or non-human animal that is likely to be treated by the composition of the present invention. In particular, subjects who are susceptible to immune dysfunction, subjects who have previously been subject to immune dysfunction, subjects who have a predisposition to immune dysfunction or subjects who show signs of immune dysfunction.

For the purposes of the present invention, the expression "effective amount" (or "therapeutically effective amount") refers to an amount of virus-like particles according to the invention necessary or sufficient to, without causing significant and unfavorable side effects for the subject, delay or stop the occurrence of an immune dysfunction, bring about improvements, reduce the severity or incidence of an immune dysfunction, or stop or cure an immune dysfunction. An effective amount may be administered prior to the onset of immune dysfunction for prophylactic or preventive action. Alternatively or additionally, an effective amount may be administered after the onset of immune dysfunction for therapeutic action.

An "excipient" means, in the present invention, any substance other than the active ingredient present in a composition conferring on it properties of stability, form (liquid, solid, capsule, etc., according to the mode of administration), taste, dissolution (for example targeted dissolution in the stomach or digestive tract), color, etc. A "pharmaceutically acceptable excipient" means more specifically an excipient which does not induce an undesirable reaction when it is administered to a subject, preferably a human. This definition includes all solvents, dispersion media, coatings, antibacterial or antifungal agents, isotonic agents and agents which delay the absorption of the active ingredient, etc. For administration to humans, the preparations must meet sterility, pyrogenicity, general safety and purity standards defined by regulatory agencies, such as the FDA's Bureau of Biological Standards.

"RNA" here means any ribonucleic acid molecule. Ribonucleic acid molecules may be natural or modified ribonucleotides, in particular to be more resistant to RNases. The RNA sequence may include stabilizing sequences that increase the half-life of the RNA in the cytosol. For example, stabilizing sequences are transcribed and untranslated sequences of the β-globin gene.

The present invention relates to a virus-like particle comprising an antigen. The virus-like particle of the present invention is intended to durably and specifically regulate the immune system, in particular to deviate the immune profile or to induce an active mechanism for regulating autoimmune responses. In order to promote the specific tolerance of the antigen, the virus-like particle of the invention further comprises an immunoregulatory molecule expressed on the surface of the particle.

Virus-Like Particles Useful in the Invention:

The virus-like particles are formed by self-assembly of at least one structural protein of viral origin such as the capsid protein or the envelope protein. These particles mimic the structure and antigenic properties of the native virion, but are unable to replicate. In particular, the virus-like particles are produced by self-assembly of structural proteins, in particular of the constituent subunits of the viral capsid and/or envelope (international patent application WO2002/34893).

According to the invention, the virus-like particles can be obtained from double-stranded DNA viruses such as herpes virus, adenovirus, parvovirus, single-stranded DNA viruses, double-stranded RNA viruses such as reoviruses, positive polarity single-stranded RNA viruses, negative polarity single-stranded RNA viruses, retroviruses. In particular the virus-like particles are obtained from the assembly of structural proteins of AAV, adenoviruses, VSV, herpes viruses.

In a particular case, the virus-like particles can be prepared from retroviruses. These may include retroviruses belonging to the family of oncoviruses, lentiviruses or spumaviruses. Within the family of oncoviruses, these include slow, non-oncogenic oncoviruses, such as MoMLV, ALV, BLV, or MMTV, and fast oncoviruses, such as RSV. Examples of lentiviruses are HIV, SIV, IVF, or CAEV.

In another particular case, the viral particle according to the invention comprises a structural protein, preferably an envelope derived from VSV (vesicular stomatitis virus), more particularly VSV-G.

The structural proteins of said virus-like particle are capsids and/or viral envelopes. The viral capsid is a multiprotein structure that encloses and protects the genetic material in a virus. The capsid is formed from copies of a single or different protein subunits. Some viruses are surrounded by a lipid bilayer envelope containing glycoproteins. This envelope helps modulate tropism and immunogenicity.

In a preferred embodiment of the invention, the virus-like particle is a synthetic retroviral particle. A retroviral particle comprises an envelope protein synthesized from an env gene, capsid proteins synthesized from the gag gene, and enzymes such as reverse transcriptase, proteases or integrase synthesized from the pol gene, associated with a viral genome consisting of two copies of RNA containing the gag/pol/env sequences. The synthetic retroviral particle comprises an envelope protein and/or a capsid protein. In particular envelopes which can be used in the present invention are envelopes of the following viruses: 4070A, RD114, 10A1, VSV, LCMV, HIV, rabies virus, or GALV. In a preferred approach to the invention, the envelope has a tropism for mammalian cells, more particularly, for human cells. In a particular aspect of the invention, the virus-like particle does not include an envelope protein.

In particular, the virus-like particle comprises the MoMLV capsid gag protein capable of self-assembling into virus-like particles.

The virus-like particles may include modified viral proteins. These proteins can be modified by, among other things, bank screening, chemical modification or genetic modification of the sequence of the natural viral protein. For example, the viral protein may be modified by amino acid substitution, addition or deletion. Viral proteins may also be covalently or non-covalently bound to the antigen and/or immunoregulatory molecule by genetic modification of the sequence of the viral protein or by chemical binding. For example, the modified viral protein may include at least a portion of the viral protein fused to the antigen or immunoregulatory molecule.

In the present invention, the virus-like particle comprises an antigen. In particular, the antigen is an autoantigen. The antigen may be exposed on the surface of the virus-like particle or contained in the virus-like particle. The antigen may be associated with the virus-like particle for example through the envelope, a fragment of the envelope, the capsid protein, a fragment of the capsid protein. In particular, the antigen can be fused through the N-terminal or C-terminal domain of the capsid protein or the fragment of the capsid protein to be contained in the virus-like particle. The antigen may also be fused to the transmembrane or anchor domain of the envelope or envelope fragment or to the GPI domain to be exposed on the surface of the virus-like particle.

In another particular embodiment, the antigen can be contained in the virus-like particle, for example by fusing the antigen to the capsid, in particular to the N- or C-terminal domain of the capsid, preferably to the C-terminal domain of the capsid protein. The antigen can be bound to the structural protein directly or via a "linker", preferably a peptide sequence. Peptide sequence means an amino acid sequence which makes it possible to bind protein subunits in such a way that the protein adopts a good conformation for the activity of the protein subunits. In particular, the "linker" peptide sequence is a sequence of 1, 2, 3, 4, 5, 10, 15, 20, 30, 40 or 50 amino acids.

In a preferred embodiment, the antigen may be contained within the virus-like particle. For example, in order for the antigen to be contained within the particle, the antigen may be fused directly or via a peptide bond to the capsid protein, preferably to the C-terminal domain of the gag capsid protein. The antigen can also be exposed on the surface of the particle or contained within the particle by means of a chemical or enzymatic reaction.

In order to promote the specific tolerance of the antigen, the virus-like particle used in the invention comprises an immunoregulatory molecule.

Immunoregulatory molecules are capable of modulating the immune response, in particular by modulating the functions of antigen presenting cells and/or regulatory T cells. In a particular embodiment of the invention, immunoregulatory molecules are molecules capable of increasing the activity of regulatory T cells (Tregs).

In a particular embodiment, the immunoregulatory molecule may be a receptor capable of modulating the immune response, in particular, capable of inducing the suppressive function of Tregs. As an example, these immunoregulatory molecules can be derived from immune-check-point receptors such as PD1 (programmed cell death 1), also known as PDCD1 or CD279), CTLA-4 (cytotoxic T-lymphocyte antigen 4, also known as CD152), Tim3 (also known as HAVCR2), TIGIT (also known as IVSTM3) or OX40. In particular, immunoregulatory molecules correspond to the extracellular domain of receptors, especially the immunoglobulin-like domain of immune checkpoint receptors such as the extracellular or immunoglobulin-like domains of PD1, CTLA-4, Tim3, TIGIT or OX40.

The immunoregulatory molecule may also be a receptor ligand such as PD1-L1 (programmed cell death ligand 1, also known as CD274).

The immunoregulatory molecules can also be cytokines such as IL-2 which is required for the generation and maintenance of Tregs.

Also, on dendritic cells, the neutralization of co-stimulation molecules such as CD80, CD86, especially after CTLA4 fixation, can block lymphocyte activation.

Immunoregulatory molecules can exercise their function by modifying the orientation of immune responses, notably towards a Th1, Th2, Th3 profile, for example for the treatment of autoimmune responses. In a particular embodiment of the invention, immunoregulatory molecules are molecules capable of activating TLRs (Toll-like receptors). Examples of molecules capable of activating TLRs are molecules comprising structures conserved in pathogens such as flagellins, unmethylated CpG DNA or RNA. For example, viral RNA can stimulate TLR7/TLR8 and flagellin can stimulate TLR5 and thus promote the orientation of responses towards a Th1 profile.

RNA capable of activating TLR, useful in the present invention, can be stabilized against degradation by RNase. In particular viral RNA can be chemically modified compared to natural RNA. The modification may consist of the replacement, insertion or deletion of one or more atoms or groups of atoms. In particular, RNA comprises at least one modified nucleotide. RNA may also include a cap of one or more modified guanosine nucleotides or a tail of several adenosines. The RNA molecules of the present invention are preferentially RNAs comprising between 2 and 1000 nucleotides, more preferentially between 8 and 200 nucleotides even more preferentially between 15 and 31 nucleotides.

The RNA can be single or double-stranded RNA. The RNA useful in the present invention is preferably viral RNA. The viral RNA may be coding or non-coding, preferably the viral RNA is non-coding. In particular, non-coding viral RNA may be derived from cytomegalovirus.

The immunoregulatory molecule may be exposed on the surface of the virus-like particle or may be contained within the virus-like particle.

The immunoregulatory molecule may be exposed to the surface of the virus-like particle, for example via the envelope, a fragment of the envelope, the capsid protein, a fragment of the capsid protein or the transmembrane or anchoring domain of a protein. In particular, the immunoregulatory molecule can be fused through the N-terminal or C-terminal domain of the capsid protein or the capsid fragment of the virus-like particle.

In a particular embodiment, in order to be exposed to the surface of the particle, the immunoregulatory molecule is preferably fused to a transmembrane domain or anchoring domain of a protein, preferably a coat protein, preferably a glycoprotein. The immunoregulatory molecule can be linked to the structural protein or to the transmembrane domain directly or via a "linker", preferably a peptide sequence. Peptide sequence means an amino acid sequence which allows protein subunits to be linked in such a way that the protein adopts a good conformation for the activity of the protein subunits. In particular, the "linker" peptide sequence is a sequence of 1, 2, 3, 4, 5, 10, 15, 20, 30, 40 or 50 amino acids. Preferably, the "linker" peptide sequence is G-G-G-G-S (SEQ ID NO: 5). The immunoregulatory molecule can also be exposed on the surface of the virus-like particle or contained in the particle by means of a chemical or enzymatic reaction.

In a particular embodiment of the invention, the immunoregulatory molecule or the extracellular domain of the immunoregulatory molecule is exposed on the surface of the particle by binding the immunoregulatory molecule or the extracellular domain of the immunoregulatory molecule to the transmembrane domain of the glycoprotein of the VSV-G (vesicular stomatitis virus) or by binding the immunoregulatory molecule or the extracellular domain of the immunoregulatory molecule to the glycophosphatidylinositol (GPI) anchoring domain of the CD59 glycoprotein. Preferably, in order to improve the exposure of the immunoregulatory molecule to the surface of the virus-like particle, the immunoregulatory molecule or the extracellular domain of the immunoregulatory molecule is linked to the glycophosphatidylinositol (GPI) anchoring domain of the CD59 glycoprotein.

The immunoregulatory molecule can be covalently or non-covalently bound, it can be bound directly or via a "linker" to a viral protein, preferably via a peptide sequence. The immunoregulatory molecule can also be linked to the virus-like particle by a chemical or enzymatic reaction.

In a particular example embodiment, a retrovirus-like particle formed by the expression of a Gag protein fused at the C-terminus to an autoantigen is provided, further comprising a glycoprotein composed of the transmembrane domain of VSV-G or an anchoring domain of the CD59 glycoprotein fused at the N-terminus to an immunoregulatory molecule such as IL-2, PD-L1 or to the extracellular domain of PD1, or CTLA-4. A linker, preferably a peptide sequence may be included between the two parts to limit stoichiometric constraints. The particle may optionally contain within it non-coding RNA molecules acting as TLR ligands. Virus-like particles can be prepared by the known methods of the art. In particular, they can be produced using encapsidation cell lines. These lines are constructed in vitro and express all the proteins necessary for the constitution and encapsidation of a viral particle. Cell lines can also be transiently transfected with the genetic elements necessary for the constitution of the viral particle. In summary, the method for preparing virus-like particles comprises a step of culturing cell lines expressing the gag and/or pol and/or env proteins as described above, and a step of recovering the particles produced by the cells. The viral particles can be purified for example by centrifugation, gradients, chromatography. The cell supernatant can also be used directly without purification step.

The present invention also relates to one or more plasmid(s) capable of producing in situ the virus-like particle as described above. The plasmid comprises a nucleic acid sequence encoding the modified viral protein of the virus-like particle, for example a nucleic acid sequence encoding an envelope protein and/or a gag protein. In particular, the plasmid comprises a nucleic acid sequence encoding a viral structural protein fused with an antigen. In particular, the plasmid codes for a capsid fused to an antigen. The plasmid may also code for a viral structural protein fused to an immunoregulatory molecule. In particular, the plasmid encodes a transmembrane domain of the VSV-G envelope or a glycophosphatidylinositol anchoring domain of CD59 fused to an immunoregulatory molecule such as IL-2, PD-L1 or the extracellular domain of PD1 or CTLA-4. The viral structural proteins making up the virus-like particle can be encoded by different plasmids Immunoregulatory molecules may also be encoded by a different plasmid than the structural proteins. Plasmids may also include other elements such as gene markers and/or the origin of replication that allow in vitro manipulations.

Treatment of Immune System Dysfunctions:

The present invention also relates to the virus-like particle as described above or one or more plasmid(s) capable of producing said virus-like particle in situ for use in the treatment of immune dysfunction.

Immune dysfunction refers to diseases caused by an inappropriate response from the immune system.

Autoimmune disease, on the other hand, is caused by an inappropriate response of the immune system against molecules or a combination of molecules that are normally present in the body. These molecules are then called autoantigens. Examples of autoimmune diseases are multiple sclerosis, type 1 diabetes, lupus, autoimmune thyroids, Crohn's disease, rheumatoid arthritis, celiac disease, myasthenia gravis or Biermer's disease (autoimmune atrophic gastritis) or autoimmune hepatitis (AIH).

Pharmaceutical Compositions and Modes of Administration:

The present invention makes advantageous use of a pharmaceutical composition comprising a virus-like particle as previously described or one or more plasmid(s) capable of producing said virus-like particle in situ. The pharmaceutical composition may also include a pharmaceutical excipient such as saline solutions, buffers, isotonic solutes. The composition may also include adjuvants or immunogenic agents.

In general, the composition includes a sufficient quantity of virus-like particles, between $10^3$ and $10^{12}$ particles, more particularly between $10^9$ and $10^{11}$ particles.

The composition can be administered to prevent immune dysfunction. Said composition of the present invention may also be administered after the onset of symptoms of immune dysfunction.

The administration of the composition can be done through the different known routes of art which can be adjusted according to antigens, pathology, biological effects, plasmid or particle. For example, the composition may be administered by parenteral injection, such as subcutaneous, intradermal, intravenous, intramuscular and intraperitoneal injection. The composition may also be administered orally, sublingually, by inhalation, by infusion.

According to an embodiment of the invention, the pharmaceutical composition or medicinal product is in solid form. Examples of solid formulations suitable for oral administration include, but are not limited to, granules, powder, capsule, tablet, ointment, gel, dissolving powder, paste, chewing gum, soft capsule or softgel.

The present invention also relates to a method for preventing, treating or reducing immune dysfunction comprising administering to a subject a sufficient amount of a virus-like particle as described above.

The subject is preferably a mammal, preferably a human. In particular this method comprises administering the composition comprising the virus-like particle to a subject.

The present invention will be better understood upon reading the following examples which illustrate the invention without limiting its scope.

EXAMPLES

Materials and Methods
Plasmids

The plasmid pGag-pol encoding the capsid of MuLV (murine leukemia virus) is obtained from the plasmid pHIT60 (Soneoka Y et al. *Nucleic Acids Research.* 1995; 23(4):628-633). The CMV promoter is replaced by a minimal CMV promoter comprising a single restriction site (SacII/XbaI) allowing cloning into the plasmid of phCMV expression.

pGagGFP codes for a Gag-GFP fusion protein under the control of an hCMV promoter. This plasmid is obtained from plasmid EPX145-68 (Garrone, P. et al. Sci. Transl. Med. 3, 94ra71-94ra71 (2011)) by inserting a PCR fragment comprising a MluI restriction site between the NruI and NheI sites. The DNA fragment synthesized by PCR and encoding GFP comprising a MluI site in the 5' domain is inserted into the MluI site to give the plasmid CMV-Gag-GFP.

The lentiviral plasmid pcppT.CMV-Gag/OVA encodes a Gag-OVA fusion protein expressed under the control of the human cytomegalovirus (hCMV) promoter and an ampicillin resistance gene. The OVA sequence is inserted into the C-terminal domain of Gag via the unique MluI restriction site (position 8689; made by Genscript®).

pGag-OVA is obtained from vector pcDNA3.1 and codes for the same fusion protein as expressed by pcppT. CMV-Gag/OVA under the control of the hCMV promoter.

pGAG-MOG is obtained by inserting the coding sequence for MOG (myelin oligodendrocyte glycoprotein) into the phCMV vector. The MOG coding sequence is obtained by PCR amplification using the 5' TGACACGCGTGCCTGTTTGTGGAGCTTCTC 3' (SEQ ID NO: 1) and 5' GCTAGCTCAAAGGGGGTTTCT-TAGCT 3 (SEQ ID NO: 2) primers. The PCR product is then inserted into the vector by cloning at the MluI and NheI enzyme restriction sites.

Different plasmids encoding different forms of recombinant murine CTLA-4 with specific anchoring sequences were prepared.

The plasmid pCTLA-4WT comprises a coding sequence for the wild-type CTLA-4 protein (NCBI Reference Sequence: nm_009843.4) inserted into the pIRES plasmid (Clontech®) using the EcoRI restriction site (position 1102).

The plasmid pCTLA-4TM codes for the extracellular domain of the murine protein CTLA-4 (SEQ ID NO: 3) (MACLGLRRYK AQLQLPSRTW PFVALLTLLF IPVFS EAIQV TQPSVVLASS HGVASFPCEY SPSHNTDEVR VTVLRQTNDQ MTEVCATTFT EKNTVGFLDY PFCSGTFNES RVNLTIQGLR AVDTGLYLCK VELMYPPPYF VGMGN GTQIY VIDPEPCPDS D F LLWILVAV SLGLFFYSFL VTAV) linked to the transmembrane and intracytoplasmic domains of the VSV-G (vesicular stomatitis virus-derived G) protein (SEQ ID NO: 4: SSIASFFFIIGLIIGLFLVLRVGIHL-CIKLKHTKKRQIYTDIEMNRLGK) and separated from the extracellular domain mCTLA-4 by a flexible G-G-G-G-S sequence (SEQ ID NO: 5).

The plasmid pCTLA-4GPI encodes the extracellular domain of the murine protein CTLA-4 comprising the transmembrane domain of CD59 (SEQ ID NO: 6: MRAQR-GLILLLLLAVFCSTAVSLTCYHCF) The plasmid pIL-$2_{TM}$ codes for the murine protein IL-2 (GenBank: AAI16874) linked to the transmembrane and intracytoplasmic domain of the VSV-G protein (SEQ ID NO: 3) by a flexible G-G-G-G-S sequence (SEQ ID NO: 5).

The plasmid pIL2GPI encodes the murine IL-2 protein linked to the transmembrane domain of CD59 (SEQ ID NO: 6).

All plasmids are prepared by bacterial culture in TB medium and purified with the "NucleoBond PC 2000 Endotoxin Free" kit (Macherey-Nagel).

Cell Lines.

HEK 293T (CRL-1573, ATCC) cells are cultured at 37° C. at 5% CO2 in DMEM medium supplemented with 2 mM L-glutamine, 100 U/mL penicillin and streptomycin and 10% inactivated fetal calf serum (Thermo Fischer Scientific).

293T-GagOVA cells are obtained by infection of HEK 293T cells with recombinant GagOVA lentiviral particles. The lentiviral particles are produced by transfecting HEK 293T cells with a recombinant GagOVA lentiviral vector ((psi)pcppT.CMV-Gag/OVA), an HIV GagPol plasmid (pCMV9) and a plasmid encoding VSV-g protein (phCMV-VSVg).

Clonal cell lines are obtained by ampicillin selection and limit dilution. Clones expressing eGFP or GagOVA are sorted on GFP fluorescence or by using anti-OVA (Agro-Bio®) and anti-MuLV Gag (clone R187, CRL-1912; ATCC) antibodies in flow cytometry after cell permeation.

Production of Virus-Like Particles (VLP)

Non recombinant VLP (VLP⁻) or VLP$^{OVA}$ (VLP$^{OVA}$) are produced in 293T or 293T-GagOVA cells, respectively. The cells are seeded in 175-cm³ culture flasks at 15·10⁶ cells per flask and co-transfected to calcium phosphate 24 h later with 50 μg of plasmids comprising pGag-pol.

Tolerogenic non-recombinant VLP or VLP$^{OVA}$ (tVLP, tVLP$^{OVA}$) are produced in 293T or 293T-GagOVA cells, respectively. The cells are seeded in 175-cm$^3$ culture flasks at 15·10$^6$ cells per flask and co-transferred to calcium phosphate 24 hours later with 50 μg of plasmids comprising pGag-pol with pCTLA-4$_{TM}$ or pCTLA-4$_{GPI}$ at a ratio of 3:1 pGag-pol/pCTLA-4 for tolerogenic VLP (tVLP) and a ratio of 1:3 pGag-pol/pCTLA-4 for OVA tVLP.

VLP$^{MOG}$ and tVLP$^{MOG}$ are produced using the same protocol with 50 μg pGAG-MOG plasmid or a ratio of 2:1 pGAG-MOG/pCTLA-4$_{GPI}$ respectively.

GFP recombinant VLP are produced in DD7 cells constitutively expressing GagGFP according to the protocol described above.

VLP$_{IL2}$ are produced in 293T cells. The cells are seeded in 175-cm$^3$ culture flasks at 15·10$^6$ cells per flask and co-transferred to calcium phosphate 24 hours later with 50 μg of pGag-pol plasmids with or without pIL2$_{TM}$ or pIL2$_{GPI}$ at a ratio of 2:1 pGag-Pol/pIL2.

After 16 or 18 hours, the medium is replaced with DMEM medium-without fetal calf serum.

After 48 hours, the cell supernatant is collected, filtered through 0.45 μm pore membranes and concentrated to obtain a purified solution of retrovirus-like particles (retroVLP). Purification of the filtered supernatant is performed by centrifugation on centricons (Centricon Plus-70, Millipore), then by ultracentrifugation at 107 170 g for 2 hours at 4° C. on a sucrose gradient (Beckman rotor SW41). The VLP are taken up in 1× PBS and their concentration is determined by the BCA method (Pierce BCA Protein, Assay Kit, Thermo scientific).

Immunoprecipitation and Western Blot.

For immunoprecipitation experiments, samples (30 μg total protein) are incubated with 1 μg murine anti-CTLA-4 antibody (clone 14D3, eBiosciences) or 1 μg anti-mIL2 antibody (ebiosciences) at 4° C. for 30 minutes and then mixed with 10 μL of pre-washed Dynabeads® G-protein coupled beads (Thermo Fischer Scientific) for 1 hour. The bead-VLP complexes are washed and the beads removed using glycine buffer (pH=2.6; Sigma Aldrich) prior to analysis by Western blot.

To perform the Western blot, samples (10 μg total VLP proteins or less for recombinant proteins) are mixed with LDS sample buffer and its reducing buffer and then analyzed by electrophoresis in 4-12% Bis Tris Gel according to the supplier's instructions (Thermo Fischer Scientific). The proteins are then transferred to PDVF membranes. Immunostaining is performed in 0.05% PBS Tween buffer with rat anti-mouse antibody (clone R187, CRL-1912 cells; ATCC) recognizing the MuLV p30 Gag capsid, rabbit polyclonal anti-OVA antibody (Agro-Bio), and rabbit polyclonal anti-MOG antibody (Thermo Fischer Scientific).

Biotinylated secondary antibodies and streptavidin-Qdot (Thermo Fischer Scientific) are used for the secondary marker. The signal is detected using Quantum ST4-3026 (Vilber Lourmat).

Mice

Seven-week-old female BALB/C (AnNR/d) mice (Laboratoires Janvier) are kept in the animal housing facility under specific pathogen-free conditions in accordance with the European Union Directive on the protection of animals used for scientific purposes. All protocols were validated by the regional animal experimentation ethics committee.

Tests on Splenic Dendritic Cells.

BALB/c mouse spleens are collected and digested for 30 minutes in RPMI 10% SVF medium (Life technologies) with 0.1 mg/mL of DNase and collagenase IV (Sigma Aldrich). CD3+, CD19+ and Ter119+ cells are removed by magnetic separation with specific biotinylated antibodies (eBiosciences) and anti-biotin beads (30 μL/100.10*6 cells; Miltenyi). The remaining cells are labelled with anti-CD11c and I-A/I-E antibodies and the CD11c+ MHC-II high cells are sorted by flow cytometry (FACS-Aria, BD). The sorted cells are incubated for 24 hours with RPMI+10% SVF+GM-CSF medium (20 ng/mL; Miltenyi)±10 μg/mL LPS (Sigma Aldrich)±VLP at different concentrations. The expression of activation markers (CD80, CD86, CD40, MHC-II) is analyzed by flow cytometry and the level of cytokines secreted into the culture supernatant is tested by ELISA.

Bone Marrow Dendritic Cell Activation Test:

Bone marrow cells collected from the tibia and femur of BALB/c mice are cultured for 8 days in RPMI medium supplemented with 2 mM L-glutamine, 100 U/mL penicillin, 100 μg/mL streptomycin, 10% inactivated fetal calf serum and 20 ng/mL GM-CSF. Every 3 days the medium is replaced. At D8, differentiated bone marrow dendritic cells are cultured for 24 hours in the presence of VLP, LPS, or medium alone as a negative control. The expression of activation markers (CD80, CD86, CD40, MHC-II) is analyzed by flow cytometry and the level of cytokines secreted into the culture supernatant is tested by ELISA.

In Vitro Proliferation of Antigen-Specific CD4+ T Cells

Splenic cells and mesenteric lymph node cells are taken from OT-II FOXP3-GFP mice expressing GFP specifically in Treg Foxp3+ and a TCR specific for a peptide derived from OVA presented by MHC-II or in TCR 2D2 mice expressing a TCR specific for a peptide derived from MOG presented by MHC-II. Non-Treg cells (Tconv; TCR+ GFP−) are enriched by negative selection using biotinylated anti-Ter119, CD19 and CD8 antibodies (BD Biosciences) and anti-biotin microbeads (30 μL/100·10$^6$ cells; Miltenyi) and then sorted by flow cytometry (FACS ARIA, BD). The cells are then labelled with the CellTrace Violet marker (OT-II CTV+ cells) (CTV, Thermo Fischer Scientific).

The splenic cells containing the dendritic cells are irradiated (25 Gy) and then incubated with the peptide OVA-II$_{323-329}$ (5 μg/mL, Genscript) or an OVA protein (200 μg/mL, Sigma Aldrich) for 1 or 4 hours respectively. Alternatively, splenic cells are incubated with a MOG$_{33-55}$ peptide (90 μg/mL Biotechne) for 1 hour.

In a 96-well plate, 10$^5$ OT-II CTV+ cells or 2D2 CTV+ cells are cultured in RPMI medium supplemented with 2 mM L-glutamine, 100 U/mL penicillin, 100 μg/mL streptomycin, 20 ng/mL GM-CSF (Miltenyi) and 10% fetal calf serum inactivated with 5·10$^5$ splenocytes pre-incubated with the antigen in the presence of 1, 5 or 10 μg/mL VLP or tVLP. After two and three days, the proliferation and activation of Tconv CTV+ cells are analyzed by flow cytometry.

Murine Model of Multiple Sclerosis

Six-week-old C57BL/6 mice (Laboratoires Janvier) were subcutaneously immunized on day 0 on both sides of the flank with a 1:1 solution of 200 μg MOG 35-55 (Tocris) emulsified in CFA (Sigma Aldrich) supplemented with mycobacteria (HKMT BD Difco) at a final concentration of 5 mg/mL. On the same day and 48 hours later, 200 ng of pertussis toxin (Enzo Life Sciences) is injected intravenously into the mice. The development of EAE was monitored for 30 days and symptoms were noted every 2-3 days. Clinical scores are evaluated on a scale of 0 to 5 as follows: 0=no abnormalities; 1=weakness of tail or hind limbs; 2=weakness of tail and hind limbs; 3=hind limb paralysis; 4=hind limb paralysis and fore limb weakness; and 5=moribund. The data are reported as a mean daily clinical score.

Tolerogenic Vaccination.

The mice received intraperitoneal injections of 30 µg tVLP once daily for 10 days, between day 15 and day 25. The mice also received an injection of PBS (Placebo) or Abatacept (CTLA-4-Ig) with the same amount of CTLA-4 included in the tVLP vaccines.

Functional Testing of $VLP_{IL-2}$

The functionality of the $VLP_{IL2}$ has been tested on CTLL-2 cells (ATCC® TIB-214™). The cells are cultured in RPMI medium supplemented with 2 mM L-glutamine, 100 U/mL penicillin and streptomycin, 10% thermally inactivated fetal calf serum, 1% HEPES buffer and 0.1% 2-mercaptoethanol (all from Thermo Fischer Scientific). $VLP_{IL-2}$ (50 µg/mL) or human IL-2 (Proleukin®, Novartis) at desired concentrations are added to the medium. Cell counts and mortality are assessed daily by counting Trypan blue cells in Malassez cells.

Flow Cytometry

The antibodies used in the experiments are listed in Table 1.

TABLE 1 list of antibodies used in flow cytometry.

| Target | Clone | Dilution | Conjugate | Supplier |
|---|---|---|---|---|
| CD4 | RM4-5 | 1:400 | Horizon V500 | eBiosciences |
| CD8 | 53-6.7 | 1:400 | Alexa Fluor 700 | BD |
| IA/IE | M5/114.15.2 | 1:400 | Horizon V500 | BD |
| CD80 | 16-10A1 | 1:400 | PE-Cy7 | eBiosciences |
| CD86 | GL1 | 1:1000 | eFluor 450 | eBiosciences |
| CD11c | N418 | 1:200 | APC | eBiosciences |
| CD25 | PC61.5 | 1:200 | PE-Cy7 | eBiosciences |
| FOXP3 | FJK-16s | 1:100 | FITC | eBiosciences |
| Fixable Viability Dye | | 1:2000 | eFluor 780 | eBiosciences |
| CD40 | HM40-3 | 1:200 | APC | eBiosciences |
| CD11c | N418 | 1:200 | PE | eBiosciences |
| mIL-2 (murine IL-2) | JES6-5H4 | 1:100 | APC | BD |
| CD152 (CTLA-4) | UC10-4B9 | 1:200 | APC | eBiosciences |
| CD3 | 145-2C11 | 1:400 | Biotin | eBiosciences |
| CD19 | MB19-1 | 1:400 | Biotin | eBiosciences |
| Ter-119 | TER-119 | 1:400 | Biotin | eBiosciences |

For in vitro studies, Live Dead eFluor®780 is added to exclude dead cells from the analysis. All flow cytometry experiments are performed on the BC LSRII cytometer and the data are analyzed using FlowJo software (Treestar Inc.).

For flow cytometric analysis of VLP, 20 µg of VLP is incubated with 5 µL of 4 µm diameter aldehyde/sulfate latex beads (Thermo Fischer Scientific) for 15 min at room temperature. PBS is added to a final volume of 1 mL and incubated for 1 hour. The beads are blocked in 20 µL of fetal calf serum for 30 minutes and washed three times and incubated with anti-CD152 or anti-mIL-2 surface antibody (eBiosciences) in PBS, 2% BSA for one hour. For intra-VLP labeling, beads are treated with PBS 1% Triton for one hour. Incubation with the primary antibody (anti-MulV p30, anti-OVA and anti-MOG) and a secondary antibody is performed in PBS 0.1% Triton. The beads are then washed and suspended in 200 µL PBS before being analyzed by LSRII flow cytometry (Beckton Dickinson).

ELISA Test mCTLA-4 is detected on the surface of VLP using the ELISA method. The 96-well flat-bottomed plates (Medisorp, Nunc) are coated with murine anti-CD152 antibodies (0.2 µg/mL, clone 14D3, eBioscience) at 4° C. overnight. After washing the wells, the non-specific binding sites are blocked with PBS 1% BSA for 1 hour at room temperature. 90 µL of sample is added to each well with 10 µL Lysis Buffer and incubated for 2 hours at room temperature.

Anti-CD152 mAb antibodies (UC10-4B9, eBioscience), peroxidase-conjugated streptavidin (Sigma-Aldrich) and tetramethylbenzidine (TMB, eBioscience) are added at room temperature for 10 min to detect mCTLA-4. The reaction is stopped by adding 100 µL HCl (1 M) and the optical density is measured at 450 nm with an automatic ELISA reading plate (DTX 880 Multimode Detector, Beckman Coulter). The mCTLA-4-His tag (Thermo Fischer Scientific) is used as standard.

mIL-2 is detected on the surface of VLP using the Ready-Set-Go mIL-2 kits (eBiosciences) according to the manufacturer's instructions. $VLP^-$ are used as a negative control.

Statistical Analysis

The statistical analysis is performed with GraphPad Prism (GraphPad software) with the Mann-Whitney U test with *$p<0.05$ representing a statistically significant difference ($p<0.01$; *$p<0.001$).

Results

1. Validation of OVA and CTLA-4 Expression by TVLP$^{OVA}$

The expression of Gag and OVA by recombinant VLP (VLP$^{OVA}$) has been validated by Western blot. The VLP$^-$ obtained from WT Gag are used as a control. Western blot analyses of the supernatants of transfected cells show the formation of retroVLP carrying the antigen of interest, in this case ovalbumin (OVA) (FIG. 3A).

Immunoprecipitation by an anti-CTLA-4 antibody shows the assembly of immunoregulatory molecules (CTLA-4) on tVLP$^{OVA}$ (revealed with an anti-Gag; FIG. 3B).

The expression of the different chimeric forms of CTLA-4 (WT, TM-VSVG or with the GPI anchoring domain) was compared in transfected cells or on VLP by flow cytometry. Non-transfected cells or VLP$^-$ were used as a negative control. After comparison of the level of expression of the different chimeric forms of CTLA-4 (FIG. 3C), it appears that the GPI(CD59b) system is optimal and will be retained in the following results. We were able to quantify the presence of the CTLA-4 domain in our preparations using ELISA and the molecule represents between 8 and 15% of the total proteins measured using the bicinchoninic acid (BCA) method (FIG. 3D).

2. In Vitro Evaluation of the Effect of tVLP$^{GFP}$ on Dendritic Cell Activation.

tVLP$^{GFP}$ or VLP$^{GFP}$ (without CTLA4) and VLP$^-$ controls were contacted with purified dendritic cells (DC) based on CD11c and MHC-IIhi expression from BALB/c mouse splenocytes (FIG. 4A). The uptake of tVLP$^{GFP}$ by purified dendritic cells is confirmed by the presence of GFP$^+$ cells after 24 hours of culture. VLP$^-$ are used as a negative control (FIG. 4B). The DC phenotype is then analyzed 24 hours after stimulation by LPS (TLR4 ligand). The results show that only tVLP$^{GFP}$ significantly and dose-dependently block the LPS-induced increase in expression of co-stimulation molecules (CD80, CD86) (FIG. 4C-E). Interestingly, the level of expression of MHC-II molecules is unaffected, not interfering with the ability of DC to present the antigen (FIG. 4E). Similar results were observed when DC are derived from bone marrow progenitor cells (FIG. 5A). An increase in the level of IL-10 could also be detected in the medium in the presence of tVLP$^{GFP}$, indicating immunoregulation directly on the dendritic cells (FIG. 5B).

3. In Vitro Evaluation of the Effect of TVLP$^-$ on the Activation of Antigen-Specific T Cells.

We evaluated whether tVLP$^-$ were able to block the activation of CD4$^+$CD25$^-$ T lymphocytes from antigen-specific (OVA) OT-II mice after contact with DC, present among splenocytes irradiated and loaded with OVA protein or OVA$_{323-339}$ peptide (FIG. 6A). Analysis of T cell proliferation with "celltrace" violet (CTV®) shows good activation of OT-II T cells in the presence of OVA$_{323-339}$ peptide alone or OVA$_{323-339}$ peptide plus VLP$^-$ (FIG. 6B). On the other hand, the addition of tVLP$^-$ leads to a significant suppression of T cell activation with a dose-dependent effect, reaching at day 3 about 80% suppression with peptide stimulation (FIG. 6C) and 40% suppression with protein. Interestingly, the immunoregulatory action of tVLP$^-$ is more effective when compared to Abatacept (hCTLA-4-Ig) treatment in equivalent amounts.

4. Suppressive Effect of TVLP$^{MOG}$ on Multiple Sclerosis Effector Cells

Figure 7A:
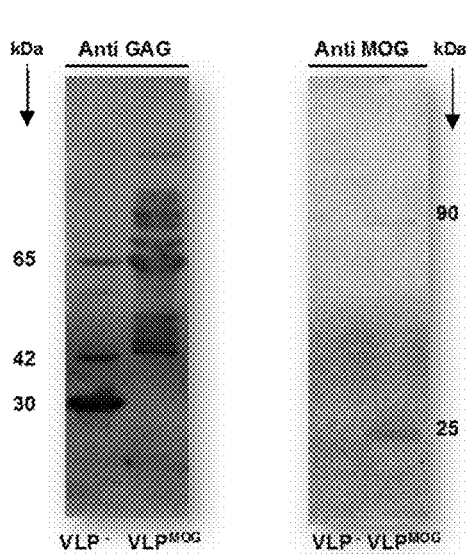
Figure 7B:
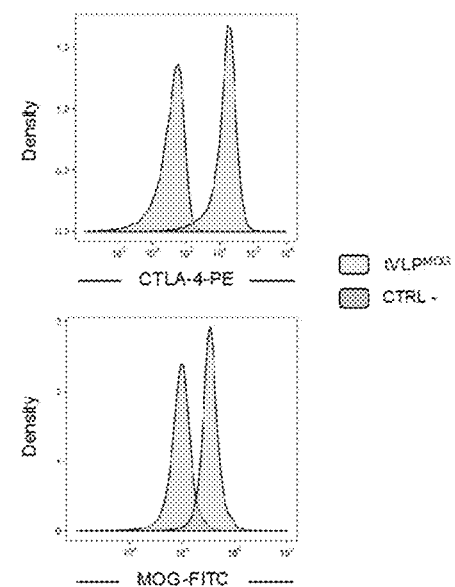
Figure 7C:
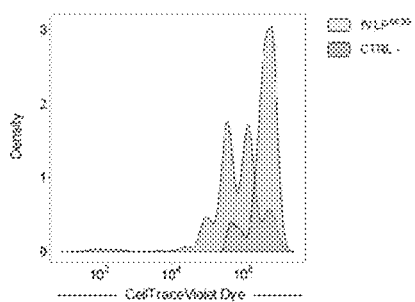
Figure 7D:
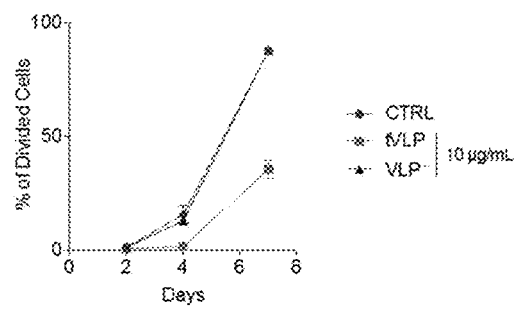
Figure 7E:
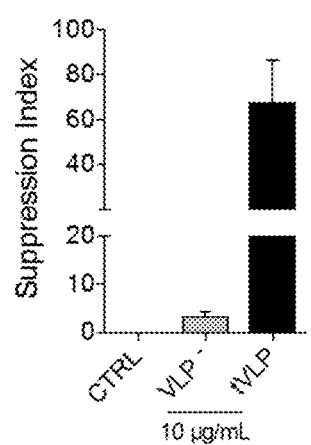
Figure 7E:
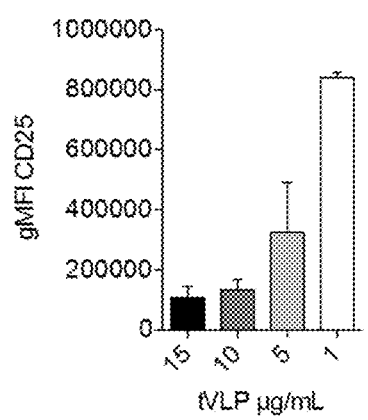

We generated retroVLPt vectorizing MOG antigen (FIG. 7A). The expression of the chimeric CTLA4 (containing the GPI domain of CD59b) on the surface of the particles and of the MOG antigen inside the particles could be observed by flow cytometry (FIG. 7B). The regulatory effect of the recombinant tVLP$^{MOG}$ could be tested by an in vitro proliferation assay with CD4+ 2D2 T cells that express a TCR receptor specific for the MOG peptide. We were able to observe that tVLP$^{MOG}$ significantly block the division of MOG-specific T cells (FIG. 7C), even after prolonged culture time (Day 7, FIG. 7D). This suppression is strong, with an index of more than 60 (FIG. 7E), and is dose-dependent as shown by the increasing decrease in expression of the activation marker (CD25) as a function of the amount of tVLP$^{MOG}$ placed in the culture.

These results constitute a first proof-of-principle of the use of tolerogenic VLP for the control of autoimmune responses and their therapeutic potential in multiple sclerosis.

5. Validation of IL-2 Expression by VLP$_{IL2}$

The expression of Gag and IL-2 by recombinant VLP (VLP$_{IL2}$) has been validated by Western blot. VLP$^-$ obtained from WT Gag and murine IL-2 are used as controls. Western blot analyses of transfected cell supernatants indicate the formation of VLP expressing IL-2 (FIG. 8A).

The presence of IL-2 was quantified using ELISA on VLP$_{IL2}$ and VLP$^-$ (FIG. 8B). The expression of the different chimeric forms of IL-2 (TM-VSVG or with the GPI anchoring domain) was compared in transfected cells or on VLP by flow cytometry (FIG. 8C). Non-transfected cells or VLP$^-$ were used as a negative control. After comparison of the level of expression of the different chimeric forms of VLP$_{IL2}$ (FIG. 8C), the GPI(CD59b) system was found to be optimal.

6. Functional Effect of VLP$_{IL2}$

Cell proliferation and percent CTLL-2 cell mortality were measured by Trypan blue in Malassez cells in the presence of IL-2 at 25 IU/mL, 50 IU/mL, VLP$_{IL2}$ or in the absence of IL-2 (SS IL-2).

Cell proliferation and the percentage of CTLL-2 cell mortality in the presence of VLP$_{IL2}$ are similar to the results obtained in the presence of cytokine IL-2 indicating that VLP$_{IL2}$ cells allow CTLL-2 cells to proliferate and are therefore functional (FIG. 9).

7. Therapeutic Effect of tVLP$^{MOG}$ in an EAE Model

FIG. 10 illustrates the therapeutic effect of tVLP$^{MOG}$ in an EAE model. The mice were treated from D15, the date on which mice immunized with the MOG antigen develop symptoms and exhibit the onset of limb paralysis. The mice received intraperitoneal injections of 30 µg tVLP once daily for 10 days, between day 15 and day 25. In control, mice were injected with PBS (Placebo) or Abatacept (CTLA-4-Ig) with an identical dose of CTLA-4. Mice treated with tVLP$^{MOG}$ had a blocked disease course in contrast to the control groups. The therapeutic effect is durable and maintained beyond the vaccination period, demonstrating tolerance induction.

FIGS. 11A and 11B show that induction of tolerance by tVLP reduces immune infiltration of the central nervous system and increases splenic Tregs. C57Bl/6 mice received daily intraperitoneal injection of tVLP or PBS (placebo) between days 15 to 25 (in bold) after induction of EAE. On day 29, spleen and spinal/brain marrow were collected and the infiltrating immune cells were isolated and analyzed by flow cytometry (FIG. 11A, inflammatory monocytes, FIG. 11B, Tregs lymphocytes). Naïve mice were included as controls. Results are presented in mean±standard deviation (n=2 mice/group). We observe a decrease in inflammatory monocytes in the central nervous system and an increase in regulatory T lymphocytes in the spleen of tVLP+ treated mice compared to control mice. The observed differences reflect a control of inflammation in the brain and spinal cord associated with recruitment of immunoregulatory cells (regulatory T cells).

The invention claimed is:

1. A virus-like particle comprising an antigen and an immunoregulatory molecule exposed on the surface of the particle, wherein the antigen is an autoantigen, the immunoregulatory molecule is linked to the transmembrane glycoprotein domain of vesicular stomatitis virus (VSV-G) or to the glycophosphatidylinositol (GPI) anchoring domain of the CD59 glycoprotein, and the virus-like particle is a synthetic retroviral particle.

2. The virus-like particle as claimed in claim 1, wherein the immunoregulatory molecule is an immune checkpoint receptor.

3. The virus-like particle as claimed in claim 2, wherein the immunoregulatory molecule comprises the extracellular domain of said immune checkpoint receptor.

4. The virus-like particle as claimed in claim 1, wherein the immunoregulatory molecule is selected from the group consisting of IL-2, IL-10 and TGF-beta.

5. The virus-like particle as claimed in claim 1 for use in the treatment of an autoimmune disease.

6. The virus-like particle for use as claimed in claim 5, wherein the autoimmune disease is multiple sclerosis, type 1 diabetes, lupus, an autoimmune thyroid, Crohn's disease, rheumatoid arthritis, celiac disease, myasthenia gravis, autoimmune atrophic gastritis, or autoimmune hepatitis (AIH).

7. The virus-like particle for use as claimed in claim 5, said particle being in the form of a pharmaceutical composition further comprising a pharmaceutical excipient.

8. A plasmid or set of plasmid(s) comprising nucleic acid sequence(s) encoding one or more modified viral protein(s) of the virus-like particle as defined in claim 1.

9. The plasmid or set of plasmid(s) as claimed in claim 8 for use in the treatment of an autoimmune disease.

10. The plasmid or set of plasmid(s) for use as claimed in claim 9, wherein the autoimmune disease is multiple sclerosis, type 1 diabetes, lupus, autoimmune thyroid, Crohn's disease, rheumatoid arthritis, celiac disease, myasthenia gravis, autoimmune atrophic gastritis or autoimmune hepatitis (AIH).

11. The virus-like particle as claimed in claim 2, wherein the immunoregulatory molecule is selected from the group consisting of IL-2, IL-10 and TGF-beta.

12. The virus-like particle as claimed in claim 2 for use in the treatment of an autoimmune disease.

13. The virus-like particle as claimed in claim 2, wherein the immune checkpoint receptor is selected from the group consisting of CTLA4, PD-1, Tim-3, LAG-3, TIGIT, and OX40.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Amorce PCR

<400> SEQUENCE: 1
tgacacgcgt gcctgtttgt ggagcttctc          30

<210> SEQ ID NO 2
<211> LENGTH: 26
<212> TYPE: DNA
<213> ORGANISM: Artificial Sequence
<220> FEATURE:
<223> OTHER INFORMATION: Amorce PCR

<400> SEQUENCE: 2
gctagctcaa aggggtttc ttagct          26

<210> SEQ ID NO 3
<211> LENGTH: 184
<212> TYPE: PRT
<213> ORGANISM: Mus musculus

<400> SEQUENCE: 3

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val
            180

<210> SEQ ID NO 4
<211> LENGTH: 49
<212> TYPE: PRT
<213> ORGANISM: Vesicular stomatitis virus

<400> SEQUENCE: 4

Ser Ser Ile Ala Ser Phe Phe Phe Ile Ile Gly Leu Ile Ile Gly Leu

```
                1               5                   10                  15
            Phe Leu Val Leu Arg Val Gly Ile His Leu Cys Ile Lys Leu Lys His
                            20                  25                  30
            Thr Lys Lys Arg Gln Ile Tyr Thr Asp Ile Glu Met Asn Arg Leu Gly
                    35                  40                  45
            Lys

<210> SEQ ID NO 5
            <211> LENGTH: 5
            <212> TYPE: PRT
            <213> ORGANISM: artificial sequence
            <220> FEATURE:
            <223> OTHER INFORMATION: Sequence flexible

<400> SEQUENCE: 5

Gly Gly Gly Gly Ser
            1               5

<210> SEQ ID NO 6
            <211> LENGTH: 30
            <212> TYPE: PRT
            <213> ORGANISM: Mus musculus

<400> SEQUENCE: 6

Met Arg Ala Gln Arg Gly Leu Ile Leu Leu Leu Leu Leu Ala Val
            1               5                   10                  15

Phe Cys Ser Thr Ala Val Ser Leu Thr Cys Tyr His Cys Phe
                            20                  25                  30
```